(12) United States Patent
Lindahl et al.

(10) Patent No.: US 8,777,946 B2
(45) Date of Patent: Jul. 15, 2014

(54) ANATOMICALLY CUSTOMIZED AND MOBILIZING EXTERNAL SUPPORT, METHOD FOR MANUFACTURE

(75) Inventors: Jan Erik Lindahl, Tkk (FI); Jari Salo, Kerava (FI); Jukka Tuomi, Tkk (FI); Roy Björkstrand, Tkk (FI); Markku Paloheimo, Tkk (FI); Kaija-Stlina Paloheimo, legal representative, Tkk (FI)

(73) Assignee: Aalto University Foundation, Aalto (FI)

( * ) Notice: Subject to any disclaimer, the term of this patent is extended or adjusted under 35 U.S.C. 154(b) by 0 days.

(21) Appl. No.: 13/499,911

(22) PCT Filed: Sep. 30, 2010

(86) PCT No.: PCT/FI2010/050756
§ 371 (c)(1),
(2), (4) Date: Jun. 27, 2012

(87) PCT Pub. No.: WO2011/042598
PCT Pub. Date: Apr. 14, 2011

(65) Prior Publication Data
US 2012/0277744 A1    Nov. 1, 2012

(30) Foreign Application Priority Data
Oct. 5, 2009    (FI) .................................... 20096019

(51) Int. Cl.
*A61F 5/04*    (2006.01)
(52) U.S. Cl.
USPC ............................................. 606/56; 606/130
(58) Field of Classification Search
USPC ........................................ 606/90, 105, 53–59
See application file for complete search history.

(56) References Cited

U.S. PATENT DOCUMENTS

| 5,122,140 A | 6/1992 | Asche et al. |
| 5,928,234 A | 7/1999 | Manspeizer |
| 6,205,411 B1 * | 3/2001 | DiGioia et al. ................. 703/11 |
| 6,355,037 B1 | 3/2002 | Crosslin et al. |
| 7,383,164 B2 * | 6/2008 | Aram et al. ....................... 703/7 |

(Continued)

FOREIGN PATENT DOCUMENTS

| WO | WO 9710775 A2 | 3/1997 |
| WO | WO 2004070573 A2 | 8/2004 |

OTHER PUBLICATIONS

Articulated external fixation of the ankle: minimizing motion resistance by accurate axis alignment, M. Bottlang, J.L. Marsh, T.D. Brown, Biomedical Engineering, The University of Iowa, Iowa City, IA 52240, U.S.A., 1999.

(Continued)

*Primary Examiner* — Pedro Philogene
*Assistant Examiner* — Lynnsy Schneider
(74) *Attorney, Agent, or Firm* — Seppo Laine Oy; Joshua P. Wert

(57) ABSTRACT

The present invention relates to an anatomically personalized and mobilizing external support, a method for manufacturing is, as well as the use of a component of an invasively attached external support in determining the path of the joint being supported. In the method according to the invention, the kinetic dynamics of the joint are measured with the aid of a component of an external support invasively attached to two bone groups, on the basis of which an external support is arranged between the bone groups.

13 Claims, 2 Drawing Sheets

(56) References Cited

U.S. PATENT DOCUMENTS

| | | | |
|---|---|---|---|
| 7,881,771 B2* | 2/2011 | Koo et al. | 600/426 |
| 2003/0191466 A1* | 10/2003 | Austin et al. | 606/54 |
| 2004/0073211 A1* | 4/2004 | Austin et al. | 606/54 |
| 2005/0020909 A1* | 1/2005 | Moctezuma de la Barrera et al. | 600/424 |
| 2005/0215997 A1* | 9/2005 | Austin et al. | 606/56 |
| 2005/0267722 A1* | 12/2005 | Marquart et al. | 703/11 |
| 2007/0161984 A1* | 7/2007 | Cresina et al. | 606/54 |
| 2009/0299368 A1* | 12/2009 | Bauer | 606/57 |

OTHER PUBLICATIONS

Pilon Fractures, Treatment Protocol Based on Severity of Soft Tissue Injury, J. Tracy Watson, MD; Berton R. Moed, MD; David E. Karges, DO; and Katrhryn E. Cramer, MD, Jun. 2000.

Two-ring Hybrid External Fixation of Distal Tibial Fractures: A Review of 47 Cases, Jukka Ristiniemi, MD, Tapio Flinkkiiä, MD, PgD, Pekka Hyvönen, MD, PhD, Martti Lakovaara, MD, Harri Pakarinen, MD, Fausto Biancari, MD, PhD, and Pekka Jalovaara MD, PhD, Jan. 2007.

Williams: "A comparison of four functional methods to determine centers and axes of rotations". Gait & Posture, Nov. 2008, vol. 28, No. 4, pp. 673-679, doi: 10.1016/j.gaitpost.200805.010 section "2. Methods" on pp. 674-675.

Yoon H.K. et al., Computer and Robotic Model of External Fixation System for Fracture Treatment, Computational Science—ICCS 2004.

* cited by examiner

ANATOMICALLY CUSTOMIZED AND MOBILIZING EXTERNAL SUPPORT, METHOD FOR MANUFACTURE

FIELD OF THE INVENTION

The present invention relates to tissue-damage rehabilitation devices and methods. In particular the invention relates to the creation of external support for damaged tissue, in order to support the tissue during rehabilitation. More specifically, the invention relates to the method, device, and use according to the preamble portions of Claims 1.

BACKGROUND ART

As is known, the care of serious damage to a synovial joint resulting from accidents is challenging. For example, falling accidents often result in serious damage to the ankle, which is caused by the ankle bone impacting the cartilage surface of the tibia, which in the worst case can even lead to the crushing of the lower end of the tibia. Recovery from injuries like those described usually takes several months. In typical care following a falling accident, the damaged ankle is repaired operatively and fixed, i.e. supported rigidly, using, for example, so-called pilon rings and similar care accessories. However, in order to recover to full functionality, the cartilage requires nutrition, the transportation of which—unlike that in other tissues—is based on the tissue being loaded in cycles, so that fluid dynamics appear inside the cartilage. The recovery of cartilage is described in detail in the publication, '*Influence of cyclic loading on the nutrition of articular cartilage*' (O'Hara B., Urban J., & Maroudas A., Ann Rheum. Dis. 1990 July; 49(7): 536-539). If mobilization that transports nutrients is not arranged, the cartilage surface repaired by the operation may be destroyed, which will be followed in a couple of years by a state corresponding to osteoarthritis, i.e. invalidity. Precisely because osteoarthritis patients are mostly young people or those of working age, such as building workers, invalidizing osteoarthritis leads to not only personal misfortune, but also a significant economic cost.

In the publication '*Articulated external fixation of the ankle: minimizing motion resistance by accurate axis alignment*' (Bottas M., March. L., & Brown T., Journal of Miomecanics, Vol. 32, No. 1, January 1999, pp. 63-70), it is stated that factors promoting recovery from, for example, the ankle-fracture injuries referred to above are protection from loads, early post-operative movement, a reduction in splinter fractures, and minimal disturbance of the injured area. For this reason, post-operative supports for damaged joints have been developed, so that in aftercare it will be possible to take into account mobilization of the joint as a precondition for recovery. However, it should be noted that, besides the mobilization of a damaged joint, its correct timing is of considerable significance in the success of rehabilitation. For example, the mobilization of an ankle must be started already two days after an operation. Correspondingly, a movement of the wrong kind can have disadvantageous consequences. It is therefore of decisive importance to find to find the joint's anatomically correct path, in order to minimize the resistance to motion and avoid sudden damage caused by the wrong kind of movement. Thus, significant expectations are directed to post-operative supports, in relation to both being able to be rapidly installed and to creating the correct type of path.

Many external supports are known. However, the majority of supports intended for the aftercare of synovial joint injuries are either rigid, i.e. the supports do not permit therapeutic movement, or supports permitting movement, the motion permitted by which is typically a rough approximation of the real movement of the joint. In a hinge joint, such the ankle, movement takes place around only a single axis of rotation, with a limited extent of movement. This is the simplest model of a moving joint, due to which it is used as an illustrative example in this connection. In other types of synovial joint, rotation and sliding in the direction of several axes or planes of movement can take place simultaneously. These can be controlled equally by means of the technology disclosed here. Rigid supports are, among others, Ilizahrov rings, which are external supports attached on both sides of the damaged joint. Ilizahrov rings are a way of implementing joint support that penetrates the tissue, i.e. it is invasive. In the method, the rings are attached to the patient's bone by using tensioning cables and bone screws. Ilizahrov rings and their use are described in greater detail in the publications '*Pilon fractures. Treatment protocol based on severity of soft tissue injury*' (Watson J. T., Moed B. R., Karges D. E., Cramer K. E. Clin. Orthop. 2000; 375: 78-90) and '*Two-ring hybrid external fixation of distal tibial fractures: A review of 47 cases*' (Ristiniemi J., Flinkkilä T., Hyvönen P., Lakovaara M., Pakarinen H., Biancari F., Jalovaara P., J. Trauma 2007; 62: 174-183), the contents of which is included in this as a reference. In addition, non-invasive rigid supports are known, such as traditional plaster casts and similar. Supports permitting movement have been created, for example, by arranged external hinge-type plates, with the aid of which an attempt has been made to imitate the movement of the damaged joint. An example of the said plate in cases like the ankle fracture described above is a kind of pedal, on top of which the base of the foot is placed and which is adjusted to permit only such a tilting movement as would be natural for a healthy ankle.

Alternative methods are known for defining the natural movement of a synovial joint. In camera-based methods, the movement is recorded by using, for example, a video camera and alignment marks, which are attached to the object to be moved. After recording the movement, the preferably digital video material is analysed using special software and the movement information obtained with the aid of the alignment marks is captured, in order to form the path of movement. This method is utilized widely, for example, in sports applications and in the film industry, for which the technology was originally developed. Because the method does not require physical contact with the patient, the method is quite user-friendly from the patient's point of view. The accuracy of the method varies from the accuracy required for making animations to the accuracy required for quality control. However, in the final resort the accuracy of the method depends on the resolution of the camera and on the measurement volume used. Typically, sufficiently accurate information is obtained by means of the method for animation of the movement of an entire limb, but this technology does not provide an answer to the movements of the bones that act as counter-surfaces in an individual joint. A drawback of the method is that, in terms of the area of the theme of the invention, the method cannot be used to determine reliably the movement of the bones under the actual tissues, but rather the movement of the tissue on top of the bones. In addition, these methods do not reveal the fine-dynamic flexing under the soft tissue, i.e. the dynamics between the bones. Because it has not been possible to accurately define the precise anatomic movement, it has also not been possible, on the basis of these methods, to design anatomically personalized external supports.

An alternative to camera-based methods are three-dimensional or radiographic methods, in which a three-dimensional model of the bones is formed on the basis of either computer tomography (CT) or magnetic-resonance imaging (MRI).

The methods are suitable for modelling the shape of an individual bone. MRI is not, however, suitable for situations in which steel screws or other attachment means in the area of the joint already attached for old injuries or installed for the care of a new injury. In the said cases, CT imaging would be a possible method, but it suffers from imaging interference caused by metals and from the great radiation stress caused to the patient.

In known applications, a damaged synovial joint and its part are modelled on the basis of CT or MRI, when a virtual kinetic model corresponding to the damaged joint is obtained. This solution has been typically used in early motion analysis studies of cases of injury, because the technology used has been readily available in a hospital environment. For example, publication US2008312659 discloses a method for manufacturing a prosthesis, in which a patient-specific image, which is used as an aid in the manufacture of the prosthesis, is formed from data obtained from MRI imaging. For its part, publication US2007118243 discloses a method, in which a computer-based model, which is exploited to manufacture implants, prostheses, and similar, is created from data obtained on the patient's anatomy in CT imaging. Though CT and MRI-based methods are indeed suitable for the manufacture of patient-specific artificial joints and other implants, the use of the said methods does not achieve sufficient accuracy as would permit preserving and saving a patient's own joint after injury. Traditionally, it has been possible to achieve an accuracy of about 10 millimeters, whereas achieving a good result would require an accuracy of at least 1 . . . 3 millimeters, preferably at least 0.5 millimeters. Typically, significant swelling also occurs in the area of a limb joint after injury, which reduces the accuracy if the definition of movement or the support is based on skin contact.

In general, significantly unknown tolerances relate to the technology used in the creation of bone models, which derive from the imaging quality and the grey-tome values available in sectioning. In addition, the joints, locations, and attitudes of three-dimensional models are fitted together visually in a 3D environment, which further reduces the method's reliability and repeatability. Tolerance errors made in the creation of bone models accumulate, when the attachment points are designed on the basis of the models. All in all, at least up until now, the CT and MRI-based three-dimensional method have not been applied, because sufficient accuracy cannot be achieved using the methods.

Thus, the problems of the prior art are related to the determining of the path of a damaged joint. Because each joint, tissue, and injury is different, a statistical approximation and present modelling methods have not been able to provide a solution for creating an anatomically personalized support. More specifically, using present post-operative external supports, i.e. supports external to the body, it has not been possible to place artificial or auxiliary joints sufficiently precisely on the paths of movement of the joint, so that the mobilization of an injured limb or similar will not succeed, due to which the cartilage of the joint will not receive nutrition reliably. As stated, in mechanical design, as is known, reference geometries can be utilized, either by creating them in a three-dimensional 3D-CAD system, or by bringing a camera-based digital geometry to the design system, by using various methods and various formats. Challenges generally arise in the combination of a reliable design geometry, referencing digitalization, and a real application. Thus, the known joint supports have been rigid, which is not optimal from the point of view of the recovery of a joint.

The external support devices on the market, which a priori permit movement to a limited extent around a single axis, are in point of departure universal-type devices. It has therefore not been possible to take into account the size of the patient or soft-tissue damage, which are important in terms of avoiding complications. In these cases, the attachment spikes must be placed in an area that has been very precisely defined beforehand, while the location of the external axis cannot be determined other than visually with the aid of transillumination. The precision then remains unavoidably poor and the path small.

It is an object of the present invention to solve at least some of the drawbacks of the prior art and to create an improved method for creating a anatomically personalized and mobilizing external support for rehabilitating a synovial joint.

SUMMARY

The object of the invention is achieved by means of a new type of method for creating an anatomically personalized and mobilizing external support for supporting a synovial joint between two bone groups in such a manner that it can be moved, in which method the kinetic dynamics of the joint are measured with the aid of a part of the external support attached invasively to at least one of the said bone groups, on the basis of which the external support is arranged between the bone groups.

According to one embodiment of the method according to the invention, the movement of the joint is measured using a co-ordinate measurement device and the measurement is performed from invasively attached auxiliary frames, which form part of the external support and CAD models of which are arranged in a CAD environment. According to the embodiment, the measurement data of the co-ordinate measurement device and the CAD models are combined in the CAD system, in order to model the path of the joint and the external support.

According to one embodiment of the invention, a CAD model is arranged of the external auxiliary joint permitting the modelled path and this is placed in the CAD environment between the auxiliary frames, on the same axis as that of the modelled path of movement, and, with the aid of the CAD models, at least one adapter component is arranged, which is fitted to combine the auxiliary frame and the auxiliary joint.

More specifically, the method according to the invention is characterized by what is stated in the characterizing portion of Claim 1.

The object of the invention is achieved, on the other hand, by means of a new type of external support to be fitted between the bone groups, which comprises at least one first external modular auxiliary frame, which is attached by invasive attachment means to the first bone group, at least one second external modular auxiliary frame, which is attached to the second bone group, at least one external modular auxiliary joint, which is arranged between the first and second auxiliary frame, as well as at least one personalized adapter component, which is arranged to connect the auxiliary joint to the auxiliary frame.

More specifically, the external support according to the invention is characterized by what is stated in the characterizing portion of Claim 1.

The object of the invention is achieved, on the other hand, by means of a new type of use, in which part of an invasively attached external support is used in defining the path of the joint to be supported.

Considerable advantages are achieved with the aid of the invention. This is because, by means of the method according to the invention, a particularly accurate model of the movement of the damaged joint is achieved, thanks to which it is possible to design, manufacture, and install a precisely anatomically personalized and mobilizing external support. Because a precise anatomical correspondence with the patient's own joint is obtained from the mobilizing external support, the movements to be performed in post-operative rehabilitation will imitate the natural path of movement of the joint. Thus, thanks to this movement, the joint will receive nutrition promoting recovery and the wrong kind of movement will not cause additional damage to the joint. In terms of the success of later rehabilitation, both the preservation of muscle control and the prevention of contraction (shrinkage) of the tendons are very important. Complete locking of a joint for even a few weeks will lead to detectable movement restrictions and also to immobilization osteoporosis. However, with the aid of the invention these problems can be reduced. The accurate patient-specific path of movement of the joint also permits the use of soft fillers as a basis for the regeneration of the structural parts of the joint. Thus, for the duration of recovery, the path of movement of an extensively damaged joint is controlled using the external support device according to the invention, in such a way that the movement takes place the whole time in a controlled manner, without a deforming force being directed to the soft medium before it has regenerated sufficiently to form a load-bearing cartilage and bone under the cartilage. At the same time, the invention permits controlled movement exercises of the joint, for example, as aftercare of ligament repairs.

Because, in the method according to the invention, it is possible to use devices, which have been demonstrated to be reliable in other connections, the performance of each sub-area of the method has been optimized separately. This is because according to one embodiment the supports to be attached to the bone group are Ilizahroz rings, which are a particularly advantageous way of attaching external structures to limbs. Correspondingly, according to one embodiment the measurement of the path of movement is performed using a co-ordinate measuring device, which has been shown in an engineering-shop environment to be suitable for even demanding quality-control and even calibration applications. Thus, the method can be implemented using very different device combinations, the parts of which have been proved to be good in other connections. Thus, the method is not dependent on new technologies untried in practice.

According to one embodiment, the external support's auxiliary joint is adjustable, so that the movement permitted for a joint that has been operated on can be adjusted as recovery progresses. For example, the bone groups surrounding an injured joint can be locked to be immobile for a couple of days after the operation, after which by adjusting the external support's auxiliary joint rehabilitation can be commenced in stages according to the conditions for recovery, in the cases of both the extent of movement and the degrees of freedom of the selected movements.

In addition, the invention permits the attachment spikes to be placed entirely freely, so that, for example, the damaged areas of the soft tissues can be left free, thus reducing the risk of complications. This also provides a possibility of choice to exploit the points achieving the best skeleton grip in the bone attachments and both to accelerate the operation as well as to reduce the amount of x-rays used in the operating theatre.

BRIEF DESCRIPTION OF THE DRAWINGS

In the following, some embodiments of the invention are examined in detail with reference to the accompanying drawings, in which.

DETAILED DESCRIPTION OF EMBODIMENTS

The method according to the present invention can be applied to the care of numerous different joint injuries. The method according to the invention is particularly suitable for, but not restricted to, the care of traumatic changes. Because joint injuries are caused to a very great extent as a result of falling accidents, the method according to the invention will be described hereinafter in the case of an example of an ankle fracture, because it is an anatomically simple subject. Of course, the method according to the invention is also suitable for creating the external supports required in the case of other joint injuries. A typical pilon fracture is associated with a falling accident that has taken place due to negligence in work safety, or in connection with a physical hobby, as a result of which the patient's ankle bone has impacted the cartilage surface of the tibia, which has resulted in damage to the joint between the ankle bone and the tibia. In the worst case, the entire under surface of the tibia will have shattered.

Figure 1:
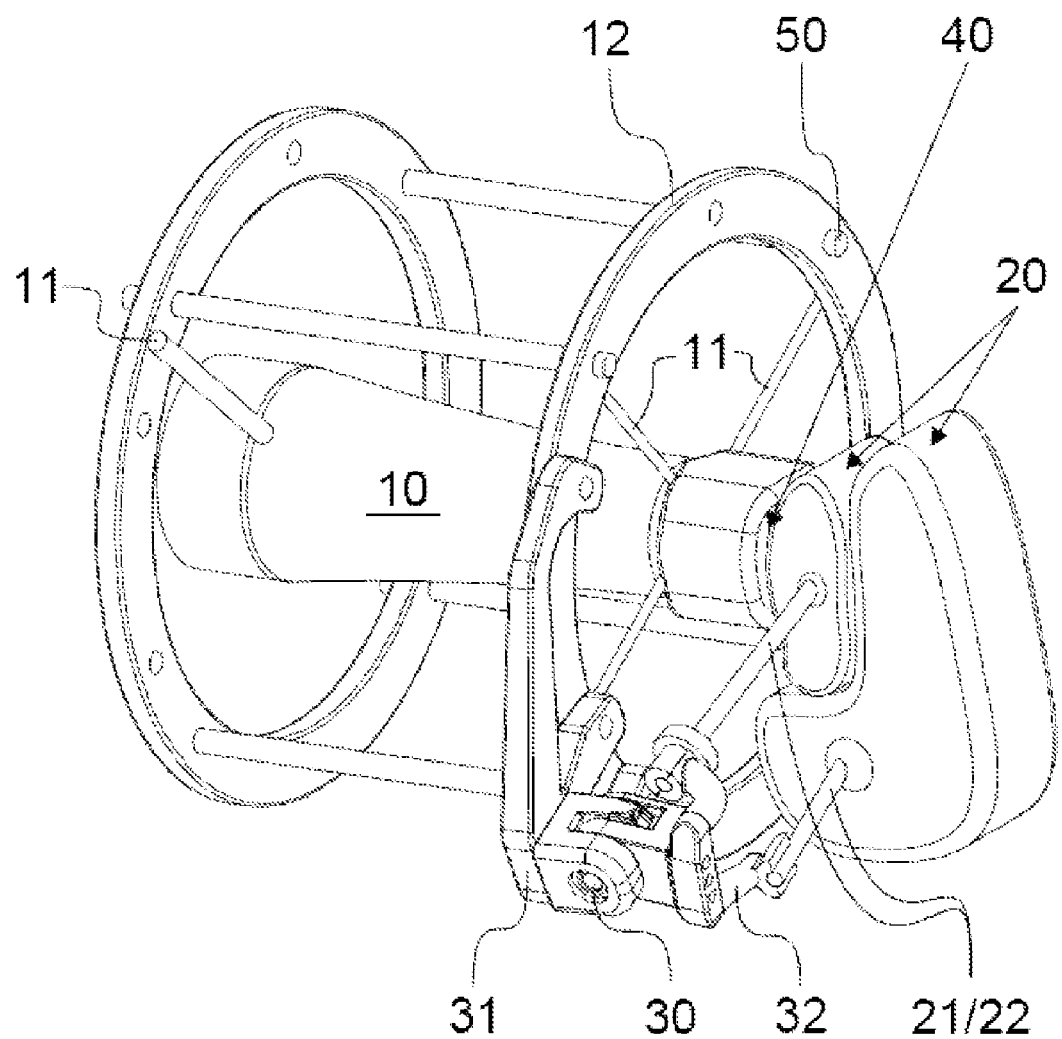
FIG. 1 presents a person's ankle, to which an external support, created using the method according to the invention, has been fitted.

As shown in FIG. 1, the damaged joint 40 is surrounded by at least two bone groups: a first bone group 10 and a second bone group 20. In the case of the example of an embodiment described here, the first bone group 10 is the tibia and the second bone group 20 is the ankle bone and the heel bone connected to it. In this connection, a group of bones, which consists of at least one bone, is regarded as being a bone group. In the case of the ankle-fracture example, the first bone group 10 thus comprises only a single bone and the second bone group 20 comprises two bones. Immediately after the injury has occurred, the patient's ankle is typically fixed, i.e. supported rigidly using splints, a plaster cast, an external attachment device (external fixator), or some other rapidly applicable means, by which movement of the ankle is prevented. Often, swelling caused by the injury prevents the fracture pieces from being immediately returned to their places and the related internal attachment using screws, spikes, plates, or other implants. If the soft-tissue situation permits, the ankle is operated on, in connection with which the pieces of cartilage are lifted off the tibia and returned to their original location. Traditionally, in the operation fixation is performed using an Ilizahrov or other rigid support device, which is known.

According to the invention, in connection with the operation, auxiliary frames 12, 22 are placed around the damaged joint 40, with the aid of which an anatomically personalized and mobilizing external support can be designed, manufactured, and installed outside the joint 40, which will permit the joint 40 to be able to be moved to the correct extent in the correct directions, according to all the directions of movement required and measured in each joint. The auxiliary frames 12, 22 are attached invasively to the bone groups 10, 20 surrounding the joint 40, for example, using bone screws or various suitable cable arrangements. In this connection, the term invasive refers to a part penetrating tissue and the term external refers to a part outside the tissue. In the example of FIG. 1, two invasive bone screws 21, which form the second attachment means, are attached to the second bone group 20. The first auxiliary frame 12, which is attached to the first bone group 10 invasively with the aid of the first attachment means, which comprise the bone screws and cables according to FIG.

1, is fitted to the first bone group 10 surrounding the joint 40. The first auxiliary frame 12 may be, for example, an Ilizahrov ring arrangement, which is easy to fit to the tibia according to the ankle embodiment. In the attachment of the auxiliary frame, the actual attachment point is, according to the invention, of no particular importance: the attachment point, for example for bone screws, is chosen on the conditions of the best possible contact and the most accommodating soft-tissue situation. Also the position and attitude of the auxiliary frame 12, 22 can be selected quite freely, but, however, in such a way that the distance of the closest point of the auxiliary frame from the coming external auxiliary joint is the smallest possible, either by visual estimate or by calculation.

As can further be seen from FIG. 1, the second auxiliary frame 22 fitted to the second bone group 20 comprises, according to one embodiment, the heads of the bone screws 21. Alternatively, the second auxiliary frame 22 could be, for example, a horseshoe-shaped ring resembling an Ilizharov ring, which is attached to the second bone group by bone screws 21. Generally, the auxiliary frame according to the invention can be an arbitrary component, which can be fixed to the bone group and to which an auxiliary joint 30 or adapter 32, which will be dealt with in greater detail later, can be fitted externally.

Figure 2:
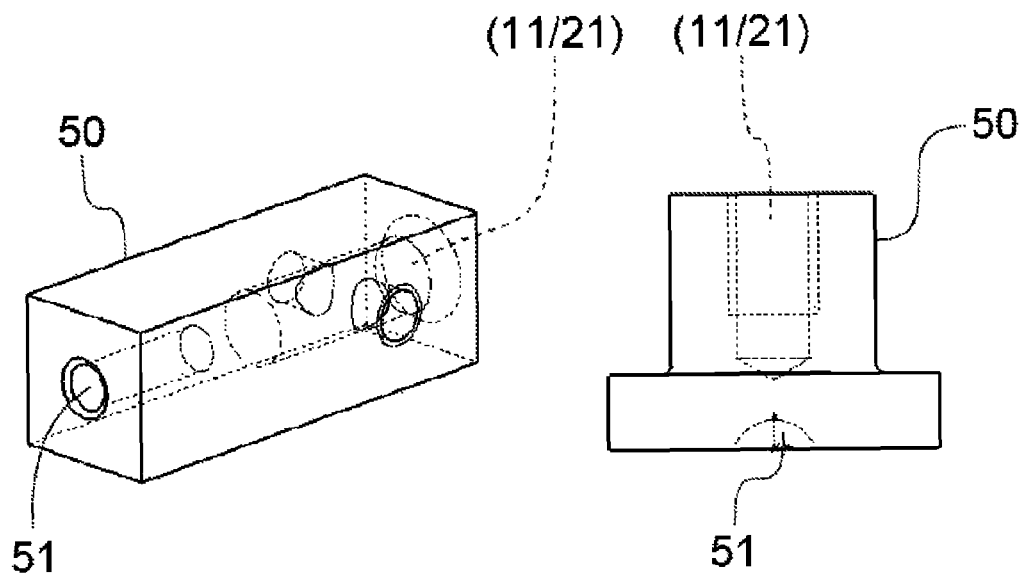
FIG. 2 presents a seating used in measurements.

Once the injured joint 40 has been repaired in an operation and the external auxiliary frames 12, 22 has been fitted to the bone groups 10, 20 surrounding the joint 40, the movement of the joint 40 is modelled for the design of a correct type of mobilizing external support. Immediately after the operation, the joint 40 is, however, fixed temporarily, for example for a couple of days, by securing the auxiliary frames 12, 22 to each other by a suitable intermediate part. According to the invention, prior to this the movement is modelled using a digitalization device, by means of which numerical and correct information is created. In this connection, the term digitalization refers to a device, by means of which movement information can be captured from a physical object and data, such as a set of co-ordinates, for processing is created. According to one embodiment, the digitalization device is a co-ordinate device, for example the MicroScribe MX, by means of which in the best case accuracy of as much as 0.05 millimeters can be obtained. Alternatively, it is possible to use, for example, a three-dimensional laser scanner, the use of which has, however, usability problems, because the application of the measurement information created using the scanner in an external set of co-ordinates is challenging. When using a co-ordinate measurement device, the measuring device and the subject of the measurement must be placed mutually in the same set of co-ordinates. In practice, the co-ordinate measurement device and the first auxiliary frame 12 are supported, in the ankle embodiment presented, for example, in an operating theatre on furniture in such a way that the distance or attitude between them does not move during the measurement. In order to facilitate the measurement, seatings 50, in which there is a recess 51 for the measuring head of the co-ordinate measurement device (FIGS. 1 and 2), are fitted to the auxiliary frames 12, 22. Thanks to the recess 51, the measuring head of the co-ordinate measurement device cannot slide away from the measuring point, in order to improve the reliability and repeatability of the measurement. As FIG. 2 shows, the seating 50 is, according to one embodiment a stud, which is attached to a hole in the auxiliary frame 12, 22, and in which there is a recess 51 or cavity with the same diameter as the measuring head, into which the measuring head must be placed in the correct attitude. The left-hand side of FIG. 2 shows the seating 50, which is equipped with a long recess 51, so that the arm of the measuring head must be correctly aligned when the measuring head touches the bottom of the recess 51. The right-hand side of FIG. 2 show a seating 50 equipped with a shallow recess 51. In both seatings 50, there is a hole on the opposite side to the recess 51, which is arranged to receive the attachment element, by means of which the seating 50 is attached to the measurement object. The first auxiliary frame 12, 22 is designed in such a way that the measurement points of the seatings 50 placed in the holes are mutually on the same plane. Alternatively, a corresponding cavity or recess 51 for the measuring head of the measurement device, promoting the measurement, can be machined or otherwise precision-manufactured in the auxiliary frame 12, 22.

In the measuring process, the intention is to obtain information of the kinetic dynamics of the joint, i.e. as to how the bone groups around the joint move relative to each other, by means of the joint. More specifically, in the measurement, the movement between the first and second bone groups 10, 20 in respect to the joint 40 is measured with the aid of the auxiliary frames 12, 22 attached to the bone groups 10, 20 by attachment means 21. In the ankle embodiment described above, the co-ordinates of the measurement points of the auxiliary frame 12 (Ilizahrov ring) attached to the first bone group 10, i.e. the tibia, are measured first. In the case of the example, at least three, preferably more, seatings 50 are attached to the first auxiliary frame 12. Because the first auxiliary frame 12 is designed in such a way that the recesses 51 in the seatings 50 are mutually on the same plane, it is easy, on the basis of the measurements to form a reference-geometry plane, which depicts the surface of the first auxiliary frame 12, to which the auxiliary joint 30 is attached. Thus, there must be at least three measurement points, in order to form each spatial plane. The measurement points are preferably more than three, because in that case measurement errors can be evened out by approximating the results computationally when forming the planes. In addition, it is good to repeat the number required, in order to eliminate measurement errors. In the case of the example above of an ankle joint, this is simplified to become a hinge joint.

Once the locations of the measurement points of the auxiliary frame 12 of the first bone group 10 have been measured, the path of the measurement point or points of the second auxiliary frame 22 relative to the first auxiliary frame 12 is measured. The path can be measured, for example, in such a way that the joint 40—in the case of the example the ankle—is moved in a natural path relative to the joint 40, during which time at least three values are measured for the measurement point of the second auxiliary frame 22. Preferably as many attitudes as possible of the joint 40 on the path are measured repeatedly, in order to eliminate measurement errors and to determine the precise length of the path. The second auxiliary frame 22 is also preferably equipped with a seating 50 receiving the measuring head, especially preferably with a seating 50 according to the example on the left-hand side of FIG. 2.

Figure 3:
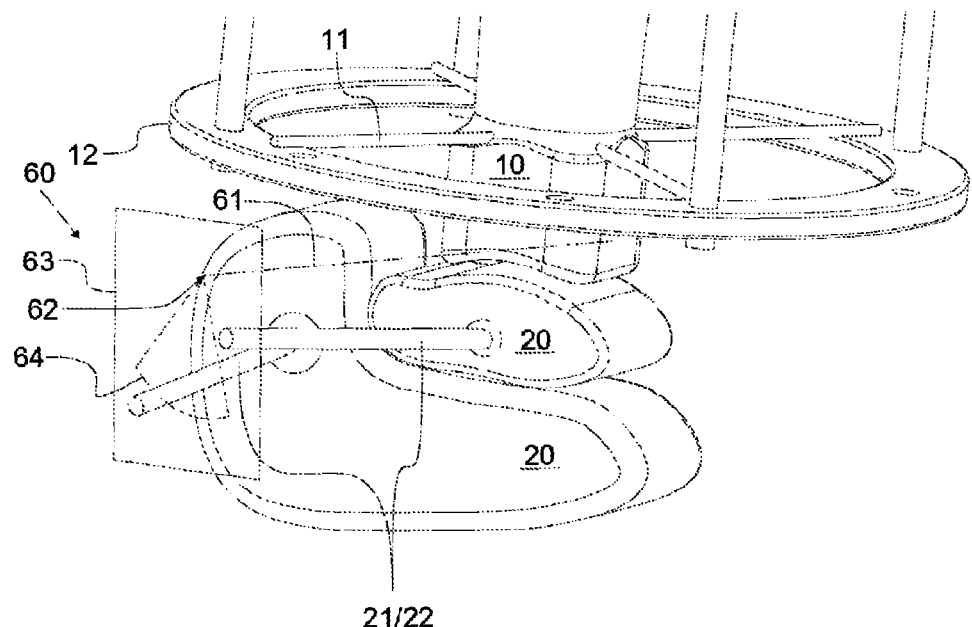
FIG. 3 presents a CAD view from the design of a support according to one embodiment of the invention.

After, or during the measurements, the measurement data is transferred to a CAD system. According to one embodiment of the invention, the measurement data is transferred from the co-ordinate measuring device directly to the CAD system, either through a common interface, or with the aid of separate software. Alternatively, the information can also be recorded in a file, from which the measurements points are loaded as points into the CAD program. Once the measurement information is in the CAD system, the kinetic dynamics of the joint 40 are modelled on the basis of the information. In the modelling of the kinetic dynamics 60, the movement of the joint 40 can be approximated and modelled very accurately on the basis of the measurements obtained from the second auxiliary frame 22, by arranging the curve 64 to run through the measurement points (not imaginary), as shown in FIG. 3. On the basis of the curve 64, in the case of a hinge joint, the plane 63 of movement and the centre point 62, axis 61, and extreme points (ends of the curve) of the rotational motion can then be determined. In a joint comprising several degrees of freedom, each rotation and sliding movement combination is defined, as well as their mutual rhythm in each plane in a corresponding manner. On the basis of the measurement results obtained from the first auxiliary frame 12, it is possible, on the other hand, to create a reference plane, relative to which the second bone group 20, i.e. the second auxiliary frame 22, moves (not shown). The reference plane is created with the aid of at least three measured points, in which case the three points are set to connect the plane. The computational creation of paths of motion, planes, and axis on the basis of measured points is, as such, known.

According to the invention, a CAD model is arranged from the auxiliary frames 12, 22. In this connection, the term arranging, refers to the fact that the CAD model is created either by procuring it in a ready-made form from a databank, in which the component has been modelled beforehand, or by forming a CAD model on the basis of an existing component. In terms of the performance of the invention, it is preferable for there to be a finished CAD model of the auxiliary frame, as well as of the components to be used, already prior to measuring, so that the operating time will not be taken up in modelling. According to one embodiment, the components used, such as the auxiliary frames 12, 22, the attachment means 21, and the auxiliary joint 30 are standard components, of which there are ready-made CAD models. The measurement points are also preferably modelled into the CAD models of the auxiliary frames 12, 22, so that the adapting of the models to the measured plane or measured axis will be easy. In addition, a CAD model is arranged of the auxiliary joint 30 (FIG. 1) used in the external support. The auxiliary joint 30 is preferably of a general-purpose model and a simple, readily available hinge-type pin joint, the path permitted by which can be limited mechanically. The hinge component can further be shaped according to modelling, in such a way that it permits sliding of the rotational centre point and the alteration of the radius of the path. This is necessary, for example, when modelling the movements of the knee.

Once the kinetic dynamics 60 of the joint 40 have been created in the CAD system, the arranged CAD models of the auxiliary frames 12, 22 are adapted to the path in the CAD system. In the case of the ankle example, the surface of the first auxiliary frame 12 closest to the second auxiliary frame 22 is placed, on the basis of the measurement results, in an attitude on the created plane (not shown), in which the measurement points coincide with each other. Correspondingly, the CAD model of the auxiliary joint 30 is placed on the path, in such a way that the axis of the auxiliary joint 30 and the axis 61 of the path coincide, so that the CAD model of the auxiliary joint 30 simulates the joint permitted by the path 64 brought into the CAD system. Preferably, kinetic centre point of the model of the auxiliary joint 30 coincides with the centre point 62 of the modelled motion. Once the length of the path is known on the basis of the model of the path, the extent of motion of the real auxiliary joint 30 is adjusted preferably to correspond to the measured natural extent of motion of the joint 40. Correspondingly, the CAD model of the second auxiliary frame 22 is aligned in place in the CAD system on the basis of the model of the path. The modelled measurement point or points are also preferably modelled in the CAD model of the second auxiliary frame 22.

Once the auxiliary frames 12, 22 and the auxiliary joint 30 have been adapted in the CAD system to the created path model, the necessary adapter components 31, 32 for connecting the auxiliary joint 30 to the auxiliary frames 12, 22 (FIG. 1) are modelled in the system. In some cases, the auxiliary joint 30 can be adapted to be connected directly to the auxiliary frame 12, 22, in which case only a single adapter component 31, 32 will be required. According to one embodiment, as shown in FIG. 1, an adapter component 31, 32 is designed between both the first and the second auxiliary frame 12, 22 and the joint 30. It is particularly advantageous to design the adapter components 31, 32 directly in the CAD system to connect the joint 30 and the auxiliary frames 12, 22, in which case drawings for manufacture can be obtained especially easily from the CAD models of the components 31, 32. According to one embodiment of the invention, the adapter components 31, 32 are manufactured using a 3D printer, or by some other instant manufacturing method, by means of which it is possible to manufacture, for example, polymer parts directly with the aid of CAD models. Alternatively, it is possible to use some other CAD-CAM system, by means of which a component of sufficient strength can be created, and which can be manufactured rapidly. For example, the component can be machined from aluminium in a machining centre, or manufactured instantly using some other technologies. The manufacture of pieces directly on the basis of CAD models is, as such, known.

Once the adapter components 31, 32 have been manufactured, they are fitted to the corresponding auxiliary frames 12, 22. The auxiliary joint 30 is fitted between the adapter components 31, 32, in which case an anatomically personalized and mobilizing external support is created outside the joint 40 between the first and second bone groups 10, 20. As stated, the auxiliary joint 30 is preferably adjustable, in such a way that the angle between it and the movement of the actual joint 40 can be adjusted. Immediately after the operation, the auxiliary joint 30 is adjusted, preferably in such a way that the movement between the first and second bone groups 10, 20 does not permit the bone groups to fix. During the period of post-operative rehabilitation, the path and angle of the movement permitted by the auxiliary joint 30 is adjusted on the basis of the CAD model of the path to be anatomically correct and the extent of the paths of motion can be adjusted as required as care progresses.

According to one embodiment, the method according to the invention is used in connection with a joint operation, in which operation a soft mass suitable for the purpose is utilized, which is arranged to differentiate in different support tissues when the joint experiences manipulation on the standard path. In the embodiment, the joint is operated on using the technique described, in which the destroyed joint surfaces are removed and is replaced by a mass like that described, which can differentiate into different types of tissue. In the embodiment, an external support according to the invention, which is particularly advantageous in connection with precisely the said mass, is arranged for the joint that has been operated on.

The embodiment described above, in which there is an anatomically personalized external support, designed, manufactured, and installed according to the invention, for repairing an ankle injury, is only one manifestation of the invention. The method according to the invention can also be applied to the rehabilitation of other joints, for instance the knee, elbow joint, or, for example, the wrist. Thus, the embodiment depicted above is not intended as a limiting specification, but rather as an exemplary description. One skilled in the art will naturally adapt the method, device, and use according to the invention to other than human patients. The present invention can also be implemented in a sequence differing from that described here. For example, the joint can be operated on and supported in the operation rigidly in a suitable manner, e.g., using a Ilizahrov ring. Once the joint permits movement, the rigid support can be removed and the invasive structures, i.e. auxiliary frames, can be utilized in measuring the movement of the joint, after which the necessary auxiliary joints and adapter components can be arranged according to the invention.

TABLE 1

List of reference numbers.

| Number | Part |
| --- | --- |
| 10 | first bone group |
| 12 | first auxiliary frame |
| 20 | second bone group |
| 21 | attachment means |
| 22 | second auxiliary frame |
| 30 | auxiliary joint |
| 31 | first adapter component |
| 32 | second adapter component |
| 40 | joint |
| 50 | seating |
| 51 | recess |
| 60 | CAD model of joint's kinetic dynamics |
| 61 | axis of rotation |
| 62 | centre point of rotation |
| 63 | plane of motion |
| 64 | path (measured points) |

The invention claimed is:

1. Method for providing a personalized and mobilizing external support for supporting moveably a synovial joint between a first bone group and a second bone group, the method comprising the steps of:
    attaching a first and second auxiliary frame to a first and second invasive attachment means respectfully, wherein the first and second invasive attachment means are attached to the first and second bone group respectively, and wherein said first and second auxiliary frames are at least partially external,
    measuring movement between the first auxiliary frame or the first invasive attachment means and the attached second auxiliary frame or the second invasive attachment means,
    determining the kinetic dynamics of the joint between the first and second bone groups based on said measurements
    producing an external adapter component based on said determined kinetic dynamics in a computer aided design (CAD) model including models of the first and second auxiliary frames, and
    attaching the produced external adapter component and an auxiliary joint to the first and second auxiliary frames.

2. Method according to claim 1, wherein the movement is measured from either the first auxiliary frame or the second auxiliary frame, which forms part of the external support, attached invasively to the bone group.

3. Method according to claim 2, wherein at least three measurement points are measured from a stationary first auxiliary frame, on the basis of which a motion reference plane is formed in a CAD environment, in which measurement points of the CAD model of the first auxiliary frame are placed in alignment with the measured points.

4. Method according to claim 2, wherein at least three different points of at least one measurement point are measured from the second auxiliary frame in correspondingly at least three different positions of the second auxiliary frame, in order to model a path in a CAD environment, in which at least one axis, relative to which the motion takes place, is modelled.

5. Method according to claim 4, wherein an axis of a CAD model of the auxiliary joint is placed in the CAD environment to correspond to the modelled axis of motion, in such a way that a kinetic centre point of the CAD model of the auxiliary joint coincides with a centre point of the modelled motion.

6. Method according to claim 1, wherein the movement is measured using a digitalization device.

7. Method according to claim 6, wherein the digitalization device is a co-ordinate measuring device.

8. Method according to claim 1, wherein movement is created relative to at least one bone group in respect to the joint and a digitalization device is used to measure points of movement between measurement points of the external parts, which are modelled as a path in a CAD environment and the CAD models of the auxiliary frames are placed in the CAD environment according to the measurement points.

9. Method according to claim 8, wherein a CAD model of the external auxiliary joint permitting the path is arranged, which is part of the external support and which is located in the CAD environment on the same axis as an axis of the modelled path, between the auxiliary frames.

10. Method according to claim 1, wherein an axis of a CAD model of the auxiliary joint is placed in a CAD environment to correspond to a modelled axis of motion, so that a kinetic centre point of the CAD model of the auxiliary joint coincides with a centre point of the modelled motion.

11. Method according to claim 10, the external adapted component is designed in the CAD environment to connect the auxiliary joint and the first auxiliary frame and a second external adapter component is designed in the CAD environment to connect the auxiliary joint and the second auxiliary frame.

12. Method according to claim 11, wherein either of the adapter components are manufactured using an instant manufacturing method.

13. Method according to claim 11, wherein the auxiliary frames and the auxiliary joint are standard components and the adapter components are personalized.

* * * * *